(12) United States Patent
Wang et al.

(10) Patent No.: US 10,488,377 B2
(45) Date of Patent: Nov. 26, 2019

(54) SYSTEMS AND METHODS TO PROCESS DATA IN CHROMATOGRAPHIC SYSTEMS

(75) Inventors: Jihong Wang, St. Joseph, MI (US); Peter Markel Willis, Benton Harbor, MI (US)

(73) Assignee: LECO Corporation, St. Joseph, MI (US)

( * ) Notice: Subject to any disclaimer, the term of this patent is extended or adjusted under 35 U.S.C. 154(b) by 915 days.

(21) Appl. No.: 14/004,450

(22) PCT Filed: Mar. 12, 2012

(86) PCT No.: PCT/US2012/028754
§ 371 (c)(1),
(2), (4) Date: Nov. 19, 2013

(87) PCT Pub. No.: WO2012/125548
PCT Pub. Date: Sep. 20, 2012

(65) Prior Publication Data
US 2014/0088923 A1    Mar. 27, 2014

Related U.S. Application Data

(60) Provisional application No. 61/451,952, filed on Mar. 11, 2011.

(51) Int. Cl.
*G01N 30/86* (2006.01)
*H01J 49/00* (2006.01)
*G06K 9/00* (2006.01)
*G01N 30/72* (2006.01)

(52) U.S. Cl.
CPC ..... *G01N 30/8675* (2013.01); *G01N 30/8644* (2013.01); *G06K 9/00543* (2013.01); *H01J 49/0036* (2013.01); *G01N 30/72* (2013.01); *G01N 30/8696* (2013.01)

(58) Field of Classification Search
CPC .................................................. G01N 30/8675
USPC .......................................................... 702/191
See application file for complete search history.

(56) References Cited

U.S. PATENT DOCUMENTS 3,488,518 A    1/1970  Taylor
7,676,329 B2 *  3/2010  Garczarek .......... G01N 30/8624
                                                    702/19
2002/0063208 A1  5/2002  Hastings
(Continued)

FOREIGN PATENT DOCUMENTS

WO      2006125864 A1   11/2006
WO   WO-2006125864 A1   11/2006
WO      2008008867 A2    1/2008

OTHER PUBLICATIONS

International Preliminary Report on Patentability dated Sep. 17, 2013 relating to International Application No. PCT/US2012/028754.
(Continued)

*Primary Examiner* — Ricky Ngon
(74) *Attorney, Agent, or Firm* — Honigman LLP

(57) ABSTRACT

A system and method for processing data in chromatographic systems is described. In an implementation, the system and method includes processing data generated by a chromatographic system to generate processed data, analyzing the processed data, and preparing and providing results based on the processed data.

64 Claims, 14 Drawing Sheets

(56) References Cited

U.S. PATENT DOCUMENTS

| | | | |
|---|---|---|---|
| 2005/0086017 A1* | 4/2005 | Wang | G06K 9/00496 702/85 |
| 2005/0261838 A1* | 11/2005 | Andreev | G01N 30/8603 702/22 |
| 2007/0095757 A1* | 5/2007 | Kaplan | G01N 30/8675 210/656 |
| 2007/0176088 A1* | 8/2007 | Li | G01N 27/62 250/282 |
| 2008/0001079 A1* | 1/2008 | Wang | H01J 49/0036 250/282 |
| 2009/0006002 A1* | 1/2009 | Honisch | C12Q 1/6858 702/20 |
| 2010/0061605 A1* | 3/2010 | Fain | G06T 7/0012 382/128 |
| 2011/0054804 A1 | 3/2011 | Pfaff | |
| 2011/0055301 A1 | 3/2011 | Du et al. | |

OTHER PUBLICATIONS

Andreev, Victor P., "A Universal Denoising and Peak Picking Algorithm for LC-MS Based on Matched Filtration in the Chromatographic Time Domain," Analytical Chemistry, American Chemical Society, US, vol. 75, No. 22, Nov. 15, 2003, pp. 6314-6326, XP001047382.

Castillo, Sandra, et al., "Algorithms and tools for the preprocessing of LC MS metabolomics data," Chemometrics and Intellignet Laboratiry Systems, Elsevier Science Publishers B.V. Amsterdam, NL, vol. 108, No. 1, Mar. 18, 2011, pp. 23-32, XP028236233.

Codrea, Marius C., et al., "Tools for computational processing of LC-MS datasets: A user's perspective," Computer Methods and Programs in Biomedicine, Elsevier, Amsterdam, NL, vol. 86, No. 3, May 3, 2007, pp. 281-290, XP022054456.

Di Marco, Valerio B., et al., "Mathematical functions for the representation of chromatographic peaks," Journal of Chromatography, Elsevier Science Publishers B.V., NL, vol. 931, No. 1-2, Oct. 5, 2001, pp. 1-30, XP004308415.

Hope, Janiece L., et al., "Evaluation of the DotMap algorithm for locating analytes of interest based on mass spectral similarity in data collected using comprehensive two-dimensional gas chromatography coupled with time-of-flight mass spectrometry," Journal of Chromatography, Elsevier Science PUblishers B.V., NL, vol. 1086, No. 1-2, Sep. 9, 2005, pp. 185-192, XP027723774.

Lommen, Arjen, "MetAlign: Interface-Driven, Versatile Metabolomics Tool for Hyphenated Full-Scan Mass Spectrometry Data Preprocessing," Analytical Chemistry, vol. 81, No. 8, Apr. 15, 2009, pp. 3079-3086, XP055050688.

Sturm, Marc, et al., "OpenMS—An open-source software framework for mass spectrometry," BMC Bioinformatics, Biomed Central, London, GB, vol. 9, No. 1, Mar. 26, 2008, p. 163, XP021031732.

WIPO, International Search Report for PCT/US2012/028754, dated Oct. 26, 2012, 6 pages.

WIPO, International Search Report for PCT/US2012/054589, dated May 3, 2013, 7 pages.

German Office Action with its English translation for Application No. 112012001185.6 dated Mar. 13, 2014.

\* cited by examiner

SYSTEMS AND METHODS TO PROCESS DATA IN CHROMATOGRAPHIC SYSTEMS

CLAIM OF PRIORITY

This application is a 371 of International Application No. PCT/US2012/028754, filed Mar. 12, 2012, which claims priority to Application No. 61/451,952, filed on Mar. 11, 2011, the entire contents of each of the above applications being incorporated herein by reference.

TECHNICAL FIELD

This disclosure relates to data processing techniques for data obtained in chromatographic mass spectrometry systems.

BACKGROUND

It is known that chromatographic mass spectrometers produce large amounts of data and that much of the data consists of noise or unwanted information. Systems and methods are desired that efficiently and accurately differentiate relevant information from noise and process same in an efficient and high resolution manner.

SUMMARY

A system and method for processing data in chromatographic systems is described. In an implementation, the system and method includes processing data generated by a chromatographic system to generate processed data, analyzing the processed data, and preparing and providing results based on the processed data.

DESCRIPTION OF DRAWINGS

Like reference symbols in the various drawings indicate like elements.

DETAILED DESCRIPTION

Figure 1:
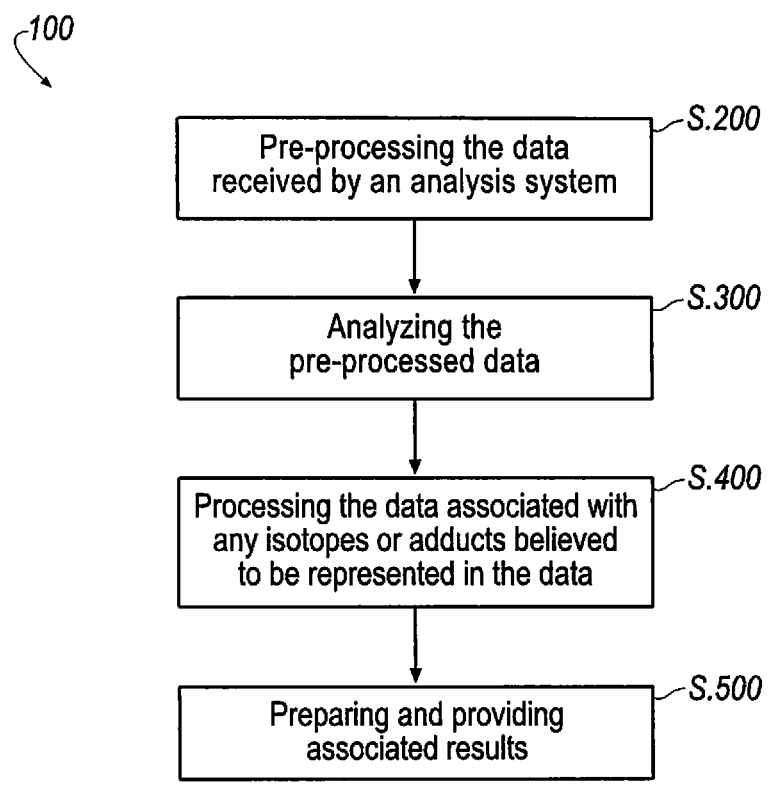
FIG. 1 depicts a general process relating to factor analysis techniques to identify and deconvolve chromatographic peaks, according to an implementation that is described in this disclosure.
Figure 2:
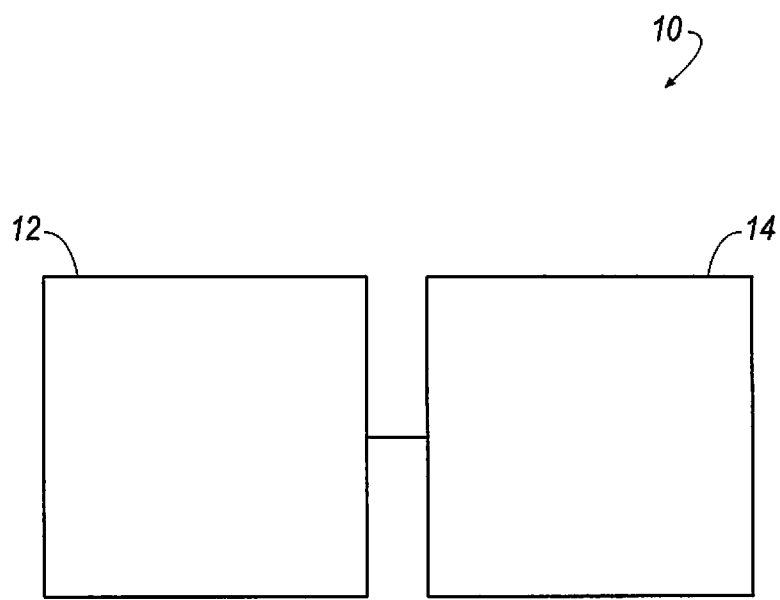
FIG. 2 is a general block diagram of a gas chromatography, mass spectrometry system.

Referring to FIG. 1, an exemplary method is disclosed for factor analysis techniques that identify and deconvolve chromatographic peaks from a chromatography, mass spectrometry system. It is to be appreciated that this method can be used in all types of chromatography systems, including liquid and gas. In an embodiment, and as illustrated, the method includes the steps of (i) pre-processing data received by an analysis system (S200), (ii) analyzing the pre-processed data (S300), (iii) processing the data associated with any isotopes or adducts believed to be represented in the data (S400); and (v) preparing and providing associated results (S500).

In an implementation, data is supplied for analysis by a data acquisition system associated with a mass spectrometer. For purposes of this disclosure, it is to be understood that the data acquisition may be a system as set forth in U.S. Pat. Nos. 7,501,621, 7,825,373, 7,884,319.

Further, prior to undergoing such analysis the data from the data acquisition system may be adjusted as set forth in U.S. Provisional Patent Application Ser. No. 61/445,674. The foregoing, and all other referenced patents and applications are incorporated herein by reference in their entirety. Where a definition or use of a term in an incorporated reference is inconsistent or contrary to the definition of that term provided herein, the definition of that term provided herein applies and the definition of that term in the reference does not apply.

In summary, the foregoing data acquisition system generally converts raw data from a mass spectrometry system into centroided mass spectral called "sticks" each representing an ion peak and consisting of intensity, an exact mass value and a mass resolution value. During construction of the sticks, the raw data from the analog-to-digital converter has undergone compression on the order of $10^4$ or $10^5:1$ and a vast majority of the acquisition noise and redundant information has been removed. The result is very sparse two-dimensional data, however chemical background noise can still remain because the objective of this data acquisition system is to forward all ion information on to the subsequent processing stages. Next, the sticks are drift corrected and gathered into clusters of statistically similar masses in adjacent retention time scans.

In an implementation, clusters with similar intensity profiles are considered to represent the various isotopes, adducts, and fragment ions from the molecular compounds eluting from the chromatographic column. In addition, there are clusters of background ions with no chromatographic structure coming from a variety of sources such as column bleed, mobile phase contaminants, atmospheric contaminants, and the like. A cluster filter may be applied to remove clusters having less than a desired minimum signal-to-noise level and the remaining clusters are then sent to a processing system for continued analysis.

Figure 3:
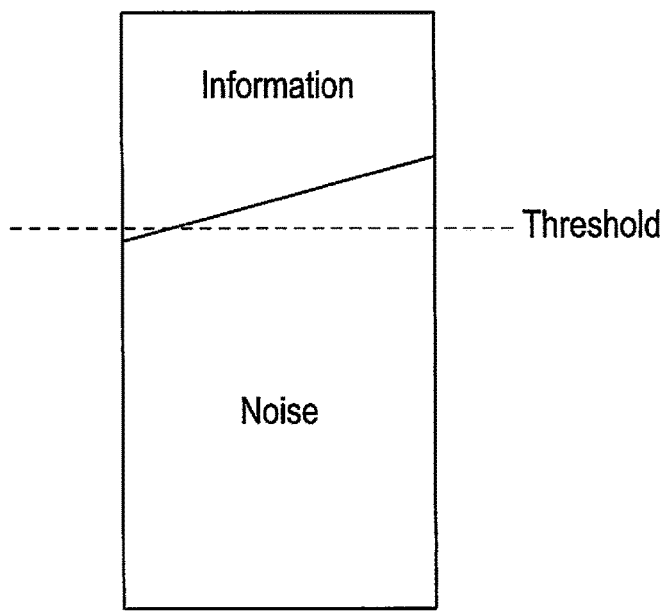
FIG. 3 illustrates a feature of the technique, according to an implementation.

It is to be understood, based on the contents of this disclosure, that at each stage of data processing, retention of good information is typically preferred at the expense of retaining some residual noise as represented by FIG. 3. In general, the described system has optimized the amount of noise that is retained to preserve data integrity.

Figure 4:
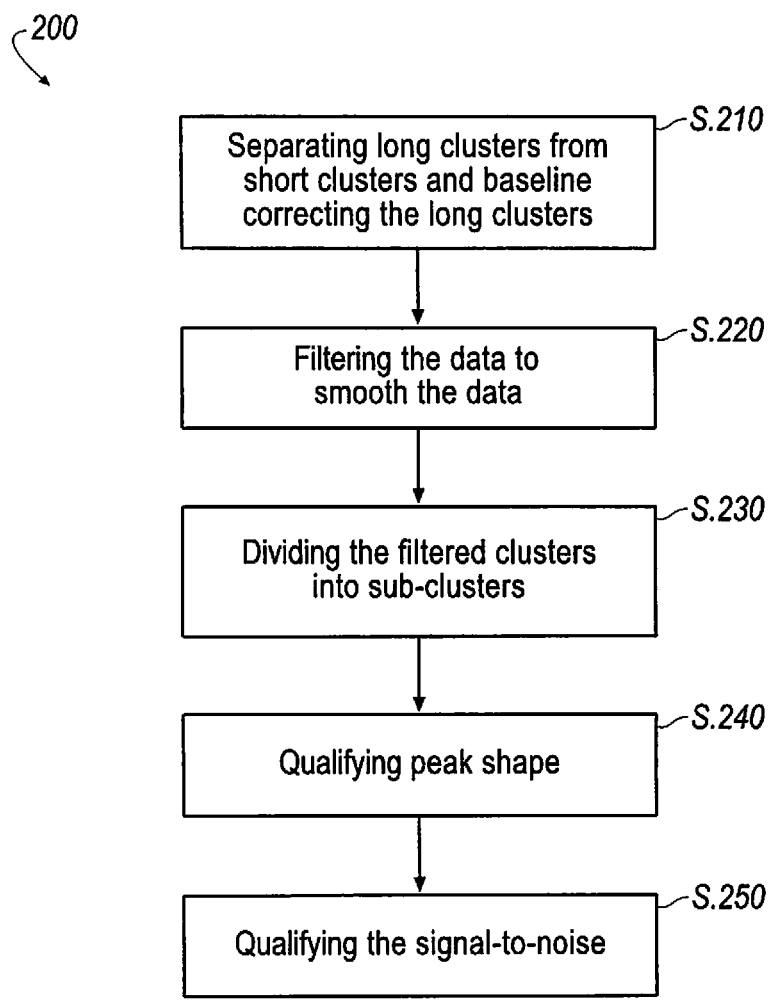
FIG. 4 represents an exemplary method for pre-processing data from a data acquisition system, according to an implementation.

FIG. 4 represents an exemplary method for pre-processing the data received by the processing system from the data acquisition system. In an implementation, processing (S200) includes the steps of separating long clusters from short clusters and baseline correcting the long clusters (S210), filtering the data to smooth the data (S220), dividing the filtered clusters into sub-clusters (S230) and qualifying the sub-clusters (S240). In an embodiment, qualification of the sub-clusters may include at least one of qualifying peak shape and qualifying the signal-to-noise, each as discussed in more detail below.

It has been found that long clusters may have durations close to the length of the entire analysis and that most of these long clusters are background ions which may effectively bias the results if they are not handled properly. Also, long clusters are often relatively intense and typically have a high noise associated with them. However, because some of this data may also contain desirable chromatographic data due to a contribution from a shared mass of an eluting compound, it is preferred to provide further analysis on the long clusters rather than extract them out altogether. Due to their elevated intensity, in an implementation, such long clusters may first undergo a baseline correction.

Figure 5:
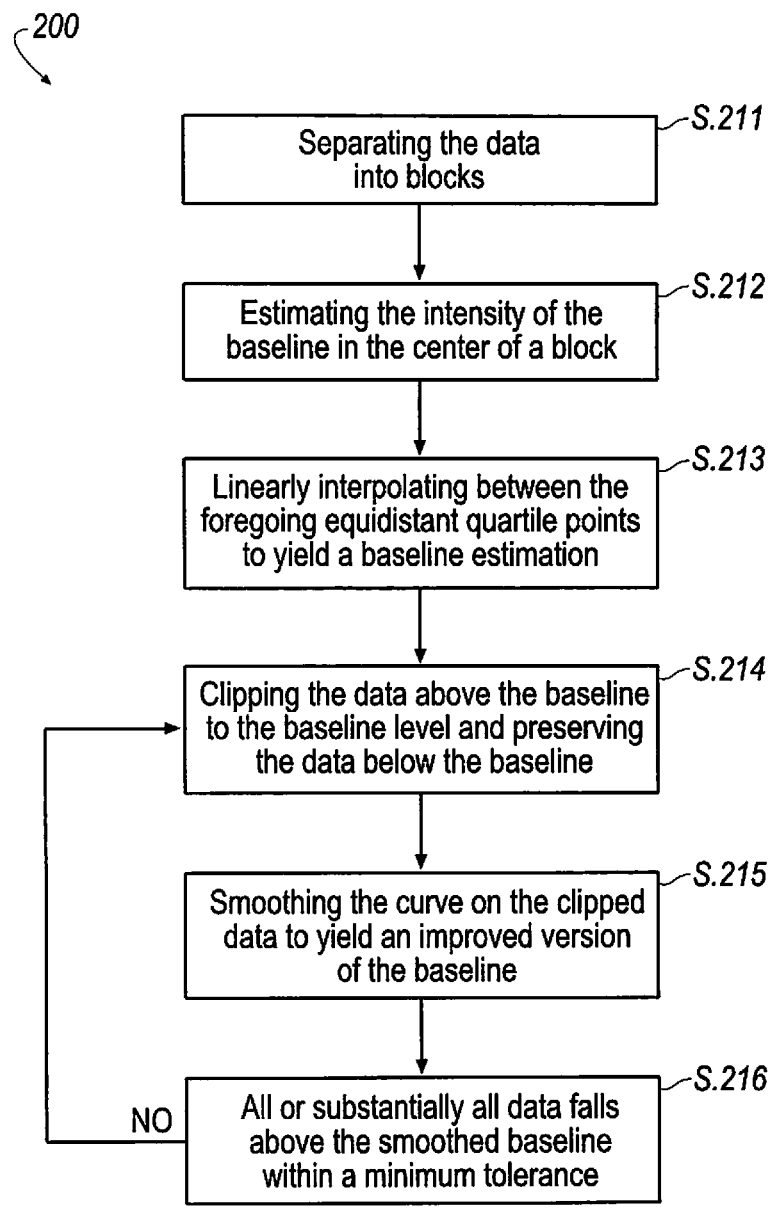
FIG. 5 represents an exemplary method of baseline correction, according to an implementation.

A method of such baseline correction will now be disclosed. In an implementation and as set forth in FIG. 5, the steps for performing a baseline correction on the data may comprise the following procedure: separating the data into blocks, the length of each block being determined as a multiple of the expected full-width half-height of the chromatographic data (S211), estimating the intensity of the baseline in the center of a block based on the intensity of the baseline in the lower quartile of that block (S212), linearly interpolating between the foregoing equidistant quartile points to yield a baseline estimation (S213), clipping the data above the baseline to the baseline level and preserving the data below the baseline (S214), smoothing the curve on the clipped data to yield an improved version of the baseline (S215) and repeating steps (S214) and (S215) until all or substantially all data falls above the smoothed baseline within a minimum tolerance. The foregoing baseline correction may be performed on each desired separated block which, in an implementation may comprise all or substantially all of the separated blocks. Similarly the correction may be applied to each long cluster which, in an implementation, may comprise all or substantially all of the long clusters.

In an implementation, the length of the block during step (S211) is estimated as five (5) times the expected full-width half-height of the chromatographic data though it is to be appreciated, based on this disclosure, that the length may be more or less than five (5) times.

As discussed, clipping the data (S214) involves smoothing the curve on the clipped data. In an implementation, a Savitzky-Golay smoothing algorithm is implemented to provide the smoothing step. Other smoothing algorithms may be employed and the invention should not be so limited thereby.

Figure 6:
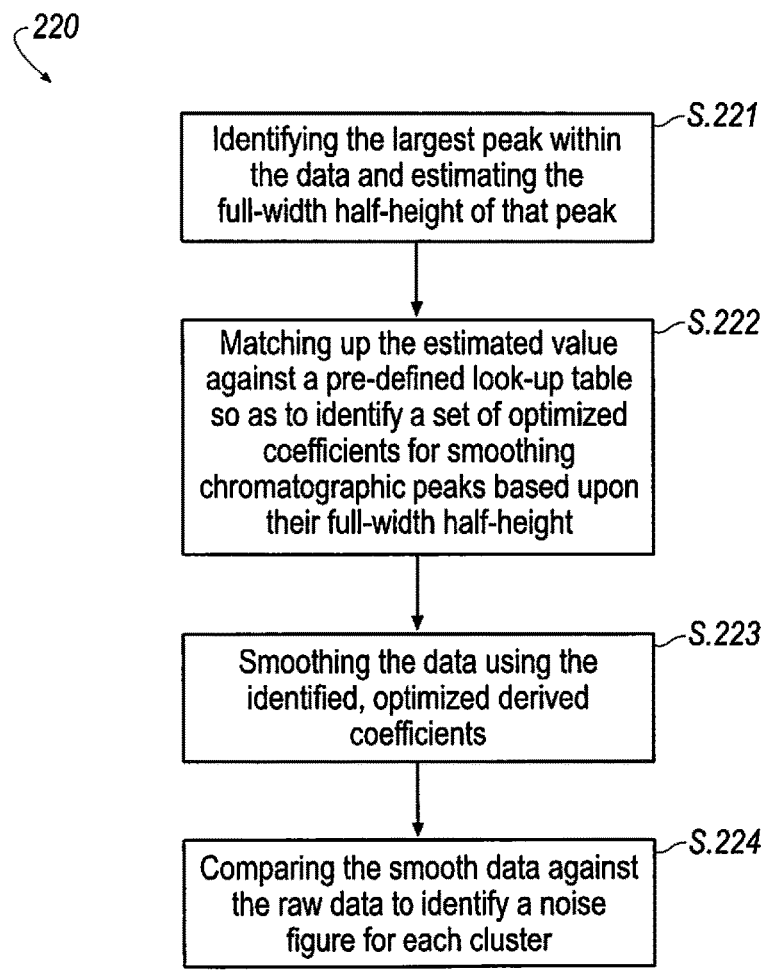
FIG. 6 identifies an exemplary implementation of a filtering process.

With continued reference to FIG. 4, the data may next be filtered to remove noise (S220). An implementation of such a filtering process is illustrated in FIG. 6. In an implementation and as discussed, an infinite impulse response filter is used in performing this step, however, it is to be appreciated based on the contents herein that other types of filters may be substituted therefor, such as a finite impulse response filter. With continued reference to FIG. 6, the largest peak is identified within the data and the full-width half-height of that peak is estimated (S221). This estimated value is next matched up against a pre-defined look-up table so as to identify a set of forward and reverse second-order infinite impulse response filter coefficients that are optimized for smoothing chromatographic peaks based upon their full-width half-height (S222). Using the identified, optimized coefficients derived in (S222), the data is smoothed (S223). Next, the smoothed data is compared against the raw data to identify a noise figure for each cluster (S224). In an implementation, the noise figure for each cluster is calculated as the standard deviation of the residual between the smooth data and the raw data. For purposes that will become evident based on this disclosure, the noise figure is retained as such will be assigned to each of the sub-clusters that are derived from a cluster in accordance with (S230). This method provides a Maximum Likelihood Least Squares estimate which facilitates an analysis that is not unduly influenced by the high intensity data and allows the low intensity data to be sufficiently represented.

Figure 7:
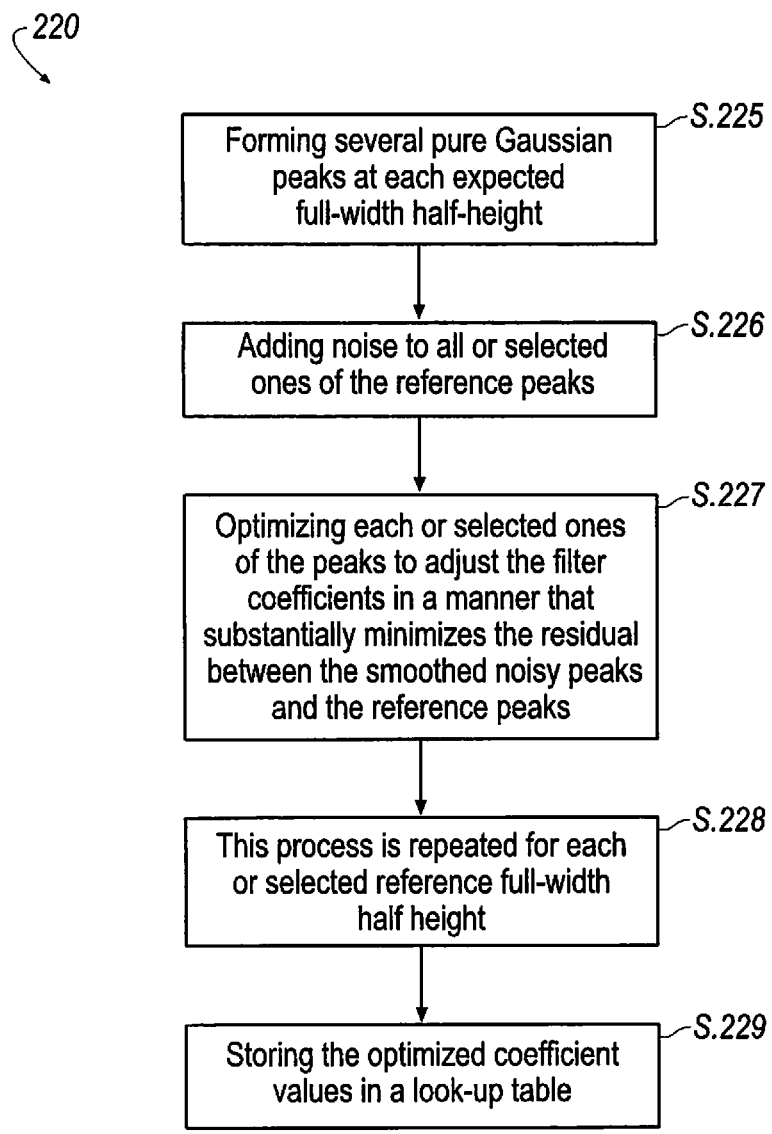
FIG. 7 depicts a representative process to identify substantially optimized coefficients, according to the principles discussed in this disclosure.

As discussed, in an embodiment the optimized coefficients are identified through the use of a look-up table at (S222). In an implementation, the optimized coefficients are pre-calculated and saved in the system for several expected full-width half-height values, before any processing occurs. FIG. 7 illustrates one way in which the coefficients may be pre-calculated.

At each expected full-width half-height, several pure Gaussian peaks are formed at (S225). In an implementation, the width of these peaks may range substantially at or between about one-third (⅓) of the target full-width half-height to three (3) times the full-width half-heights and they are stored as reference peaks. Noise is next added to all or selected ones of the reference peaks at (S226). In an implementation, the noise may be white noise and added according to a Gaussian distribution to each of the peaks. Each or selected ones of the peaks are then optimized to adjust the filter coefficients in a manner that substantially minimizes the residual between the smoothed noisy peaks and the reference peaks at (S227). Optimization (S227) may be provided using a non-linear Levenburg-Marquardt method. During the optimization, the coefficients are constrained to produce a stable impulse response. This process is repeated for each, or selected, reference full-width half heights (S228) and the optimized coefficient values are stored in a look-up table (S229). In an implementation, the impulse responses of the exemplary resulting smoothing filter resembled those of a sinc filter, where the width of the primary lobe of the filter is approximately one-half that of the target full-width half-height. Using this implementation, peak shape and structure may be substantially preserved and the number of detected false positive peaks may be substantially minimized.

Referring back to FIG. 4, the filtered clusters may be divided into sub-clusters (S230). In an implementation, the filtered cluster data is examined to identify each instance where the minimum point in a valley (situated between two peaks or apexes) is less than a defined intensity of the proximate peaks. As an example, the peak intensity may be selected to be at or around one-half (½) of the intensity of one or both of the proximate peaks. Once identified, the valleys are recognized as cluster cut points, thereby separating the cluster into one or more sub-clusters. As will be appreciated, the number of divided sub-clusters will depend on the amount of cluster cut points of a given cluster.

Figure 8:
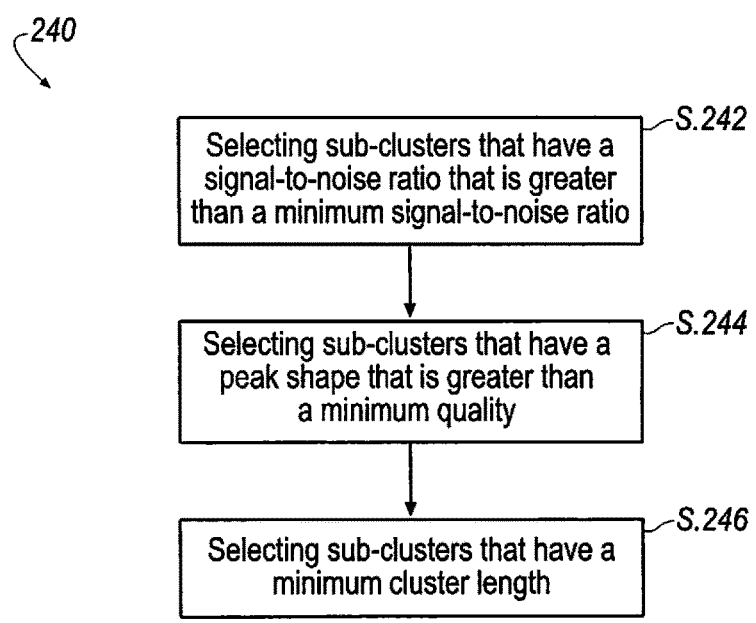
FIG. 8 illustrates a representative process that may be used to qualify peak shapes of sub-clusters, according to an embodiment.

FIG. 8 illustrates a representative process that may be used to qualify peak shape of sub-clusters (S240). This process may help to ensure that the relevant sub-cluster contains chromatographic information. In practice, some of the sub-clusters may contain data that does not contain chromatographic information, referred to hereinafter as outliers. It is preferred to extract and dispense of as many of the outliers from the data as practicable without removing relevant data. In an implementation, one or more of the following techniques may be used to separate the desired sub-clusters from the outliers: (i) selecting sub-clusters that have a signal-to-noise ratio that is greater than a minimum signal-to-noise ratio (S242), (ii) selecting sub-clusters that have a peak shape that is greater than a minimum quality (S244), and (iii) selecting sub-clusters that have a minimum cluster length (S246). In an implementation, the minimum cluster length is selected at or between 3-8 sticks, at or between 4-7 sticks, at or between 3-7 sticks, at or between 4-8 sticks, at or between 4-6 sticks or 5 sticks. Other minimum cluster lengths may be used. In an implementation, each of the separation processes may be used. For ease of disclosure, this disclosure will discuss an embodiment in which all of the processes are used as depicted in FIG. 8. Further, whichever separation processes are used, this disclosure should not be limited to the order in which they are processed.

An exemplary process for selecting sub-clusters that have a signal-to-noise ratio that is greater than a minimum or threshold signal-to noise ratio (S241) is provided. In an implementation, the threshold ratio may be selected as the lesser of a hard coded value and a user defined value. As an example, the threshold may be at or around ten (10). Among other techniques, noise may be measured as the pre-defined acquisition noise of one-fourth (¼) ion area or the standard deviation of the residual between the original cluster data and the smoothed cluster data. It is to be understood, however, that sub-clusters with a ratio under the threshold may still be used in the factor analysis if they are isotopes or adducts of the qualifying peaks.

It may be desired to further trim the sub-clusters that have a signal-to-noise ratio that is greater than the threshold as they may still contain redundant data or noise. One trimming method involves trimming the baseline of such sub-cluster from both the left and the right side of the peak. In an implementation, the raw data within the sub-cluster is scanned from one or both of the ends to the center—the location where the intensities (left/right) rises above a threshold becomes a new end of the sub-cluster and the baseline data is discarded. In an implementation, the threshold intensity is four (4) times the standard deviation of the sub-cluster noise.

Figure 9:
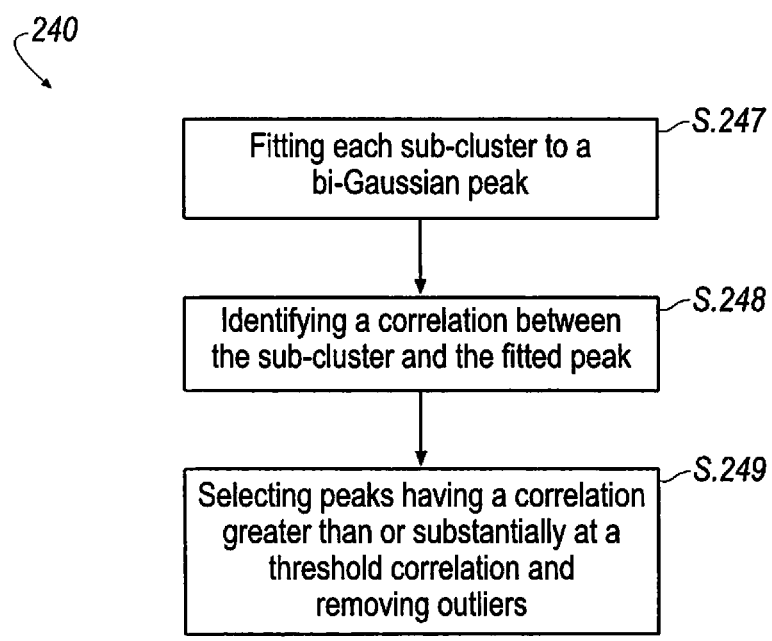
FIG. 9 recites a method in which generally extraneous data can be removed from sub-clusters to refine the data, according to an implementation.

As previously described, another technique to identify desired sub-clusters and eliminate outliers is to select sub-clusters that have a peak shape that is greater than a minimum or threshold quality (S244). In an implementation, the threshold quality may be based on the assumption that chromatographic peaks have a general shape that can be reasonably modeled, preferably, using a bi-Gaussian curve—though the invention should not be so limited thereby. A bi-Gaussian curve is preferred over other peak shapes such as Pearson IV for speed and stability of fitting. Accordingly, in an embodiment and as depicted in FIG. 9, each sub-cluster is first fit to a bi-Gaussian peak (S247). A correlation between the sub-cluster and the fitted peak is identified (S248). Peaks having a correlation greater than or substantially at a threshold correlation are selected, those having less than the threshold correlation are identified as outliers (S249). In an implementation, the threshold correlation may be 0.6, preferably 0.8.

Based on this disclosure, it is to be appreciated that each sub-cluster may be considered to contain a single chromatographic peak even though it is appreciated that such could be a shared mass composite peak due to combined information from two or more coeluting compounds, a phenomenon which can be deconvolved as further discussed below.

Referring back to FIG. 1, the data that was pre-processed in accordance with the foregoing now undergoes analysis in (S300). In this step, a method is disclosed to determine the number of significant factors for factor analysis and to provide initial seed estimates of those factors. Application of factor seeding discussed herein yields a method in which the factor analysis is prevented from unduly focusing on local minima. As a result, results can be obtained quickly with higher accuracy and resolution.

Figure 10:
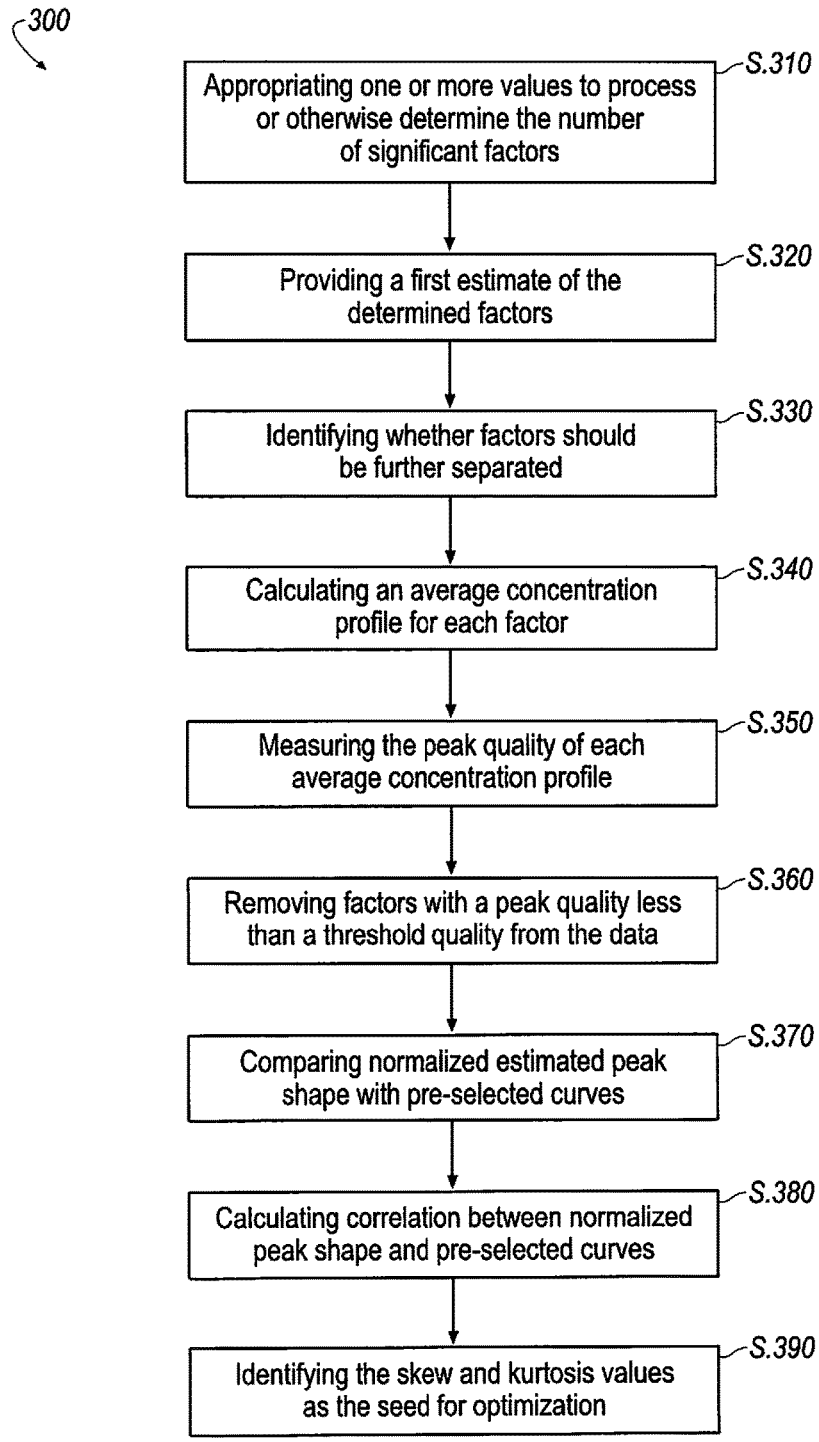
FIG. 10 depicts a seeding method according to aspects of implementations described herein.

In an embodiment and as illustrated in FIG. 10, the disclosed seeding method involves appropriating one or more values to process or otherwise determine the number of significant factors at (S310) and control the deconvolution. In an embodiment, values that may be used include, among others, the degree of chromatographic resolution, the peak overlap or peak correlation threshold and the minimal quality of resulting factors. The values may be user-selected, pre-defined or dynamically generated based on analytic results during a pre-seeding process.

In an embodiment, a multi-pass process can facilitate the factor determination. A two pass process will now be discussed but it is to be appreciated that, based on this disclosure, variant pass processes may be used and the invention is entitled to its full breadth. Further, a two-pass process may be optional such that a single pass may be used upon a determination that results from such single pass are sufficient. In summary, this process facilitates an elimination of lower quality peaks when determining factors as such peaks can blur the results, or otherwise slow down the process. As discussed later, however, some or all of the eliminated peaks can be joined at a later time in the process if such peaks are determined to be related to isotopes or adducts.

Figure 11:
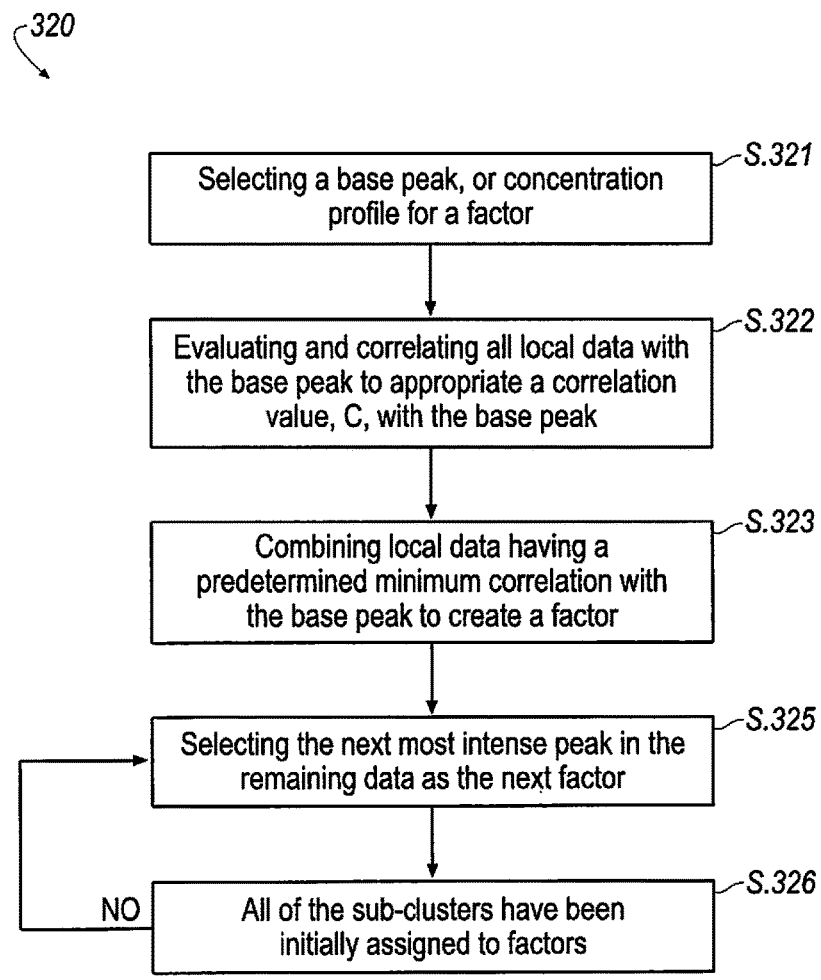
FIG. 11 illustrates a process for factor identification, in accordance with described embodiments.

In an implementation, a first pass is used to provide a first estimate of the determined factors (S320). As illustrated in FIG. 11, this pass may begin by selection of a base peak, or concentration profile for a factor (S321). The base peak may be selected manually or automatically such as through an implementation of algorithmic function or the like. In an embodiment, the most intense sub-cluster peak in a data set is selected as the base peak, as it may be assumed that such peak is likely to best represent a pure chemical, as compared to sub-cluster peaks that are comparatively less intense. In an implementation, the selected sub-cluster peak is selected as a base peak or concentration profile for a factor.

Following the selection of the base peak, all local data (e.g., the sub-clusters that may intersect this base peak) are evaluated and correlated with the base peak to appropriate a correlation value, C, with the base peak (S322). Known correlation methods may be used. In an embodiment, local data having a predetermined minimum correlation value are combined with the base peak to create a factor (S323). An initial estimate of the spectra, S, may then be specified for the identified factor (S324).

Next, the most intense peak in the remaining data is selected as the next factor and again, correlated data is combined in accordance with the process described above (S325). This process continues until all of the sub-clusters have been initially assigned to factors.

A second pass (S330) may now be employed whereby the factors from the first pass are further analyzed and a determination is made as to whether a single factor identified in the first pass can, or should, be further separated into individualized factors. During this step, a correlation parameter and a related confidence interval may be used to separate data which may have been mistakenly merged in the first pass. In an implementation, the correlation parameter may be user identified or pre-defined.

Figure 12:
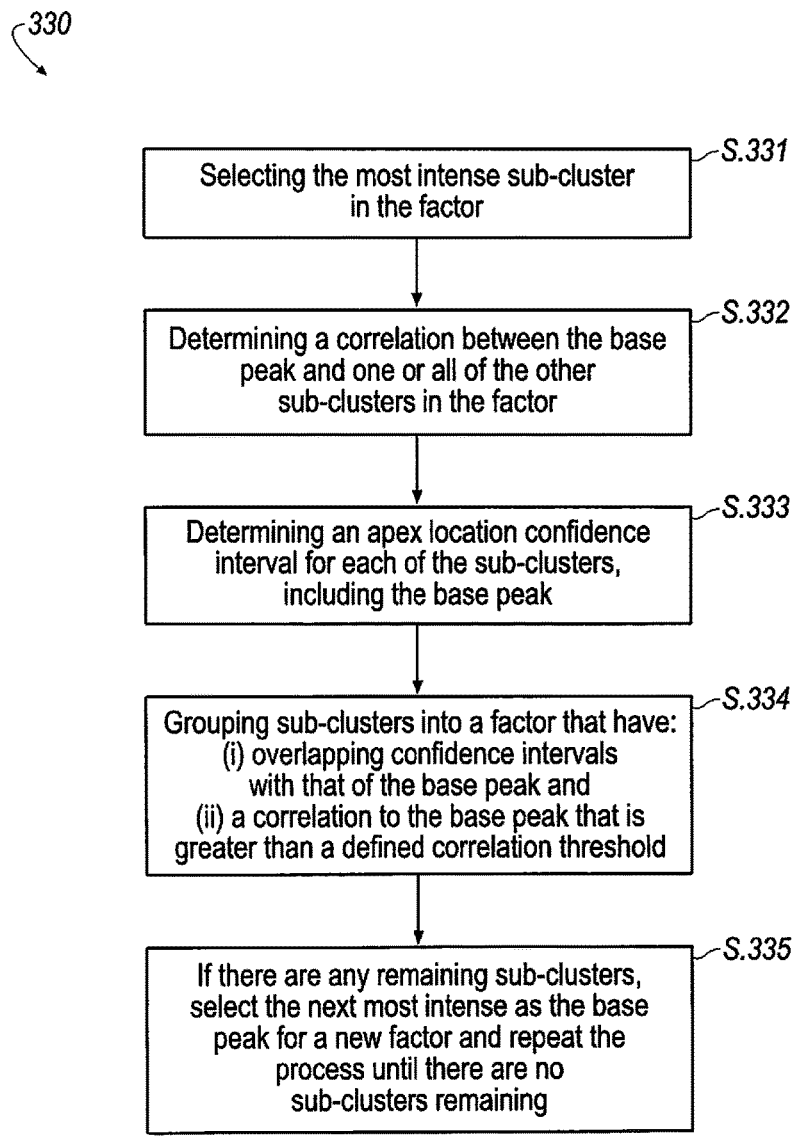
FIG. 12 depicts a comparison of M versus peak correlation threshold in an exemplary system.

FIG. 12 exemplifies an implementation that may be used in such a second pass (S330). As depicted, the most intense sub-cluster in the factor is selected (S331) which will be identified as the base peak, though other terms may be used. A correlation is calculated between the base peak and one or all of the other sub-clusters in the factor (S332). An apex location confidence interval may also be calculated for each of the sub-clusters, including the base peak (S333). An exemplary confidence interval determination may be:

$$CI = ApexLocaation \pm \frac{M * PeakWidth}{\sqrt{S/N}}$$

In the foregoing equation, (i) M references a sigma multiplier and relates to the number of desired standard deviations, which may be related to a peak correlation threshold as discussed below, (ii) PeakWidth is the full-width-half-height of the sub-cluster peak of which the confidence interval is desired, (iii) S/N is the signal to noise ratio for the sub-cluster which is calculated as the ratio of the peak height to the peak-to-peak noise of the sub-cluster, and ApexLocation is the time location of the apex of the peak. While an exemplary confidence interval determination is disclosed, other calculations may be used and, unless specifically disclaimed, the invention should not be limited to the disclosed example.

Figure 13:
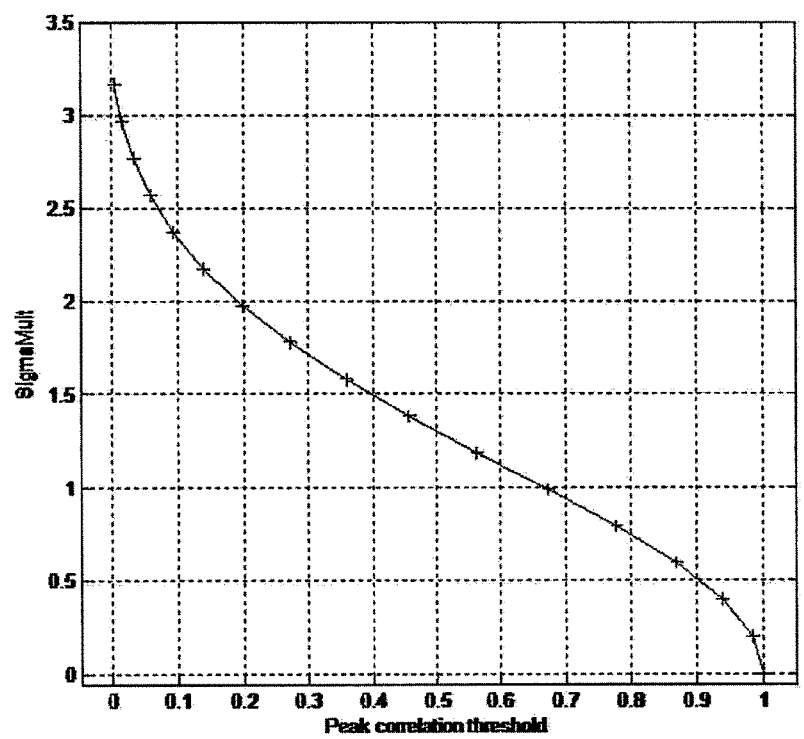
FIG. 13 graphically demonstrates M versus peak correlation threshold, in an implementation.

If preferred and as previously set forth, in an implementation, M can be functionally related to the peak correlation threshold as depicted in FIG. 13. FIG. 13 graphically demonstrates M versus peak correlation threshold based on measurements of the correlation and confidence interval overlap of two Gaussians time-shifted in varying amounts. The plotted relationship may be used so that when either peak correlation threshold or M is identified, the other value may be automatically derived based on this demonstrative relationship. Alternatively, in an implementation, it may be desired to provide independent peak correlation threshold and M.

In an implementation, a high confidence will tend to have a large M (at or between 2-4, or at or around 3) and a wide confidence interval. And for very intense peaks (e.g., those tending to have an elevated signal to noise ratio), the confidence interval may tend to be narrow because there are a sufficient number of ions to make the uncertainty of the apex location very small. For example, if a sigma multiplier of 3 is used for a base (or sub-cluster) whose apex is located at time 20, the peak has a width of 2, a height of 2560 and a peak-to-peak noise of 10, then the confidence interval is 20±0.375 for the apex location of the base peak. All sub-clusters whose confidence intervals overlap the confidence interval of the base peak and whose correlation to the base peak is greater than the user specified peak correlation threshold are grouped together into a factor (S334). If desired, if there are any remaining sub-clusters, the most intense of the remaining sub-cluster is selected as the base peak for a new factor and the process is repeated until there are no sub-clusters remaining (S335). The amount of new factors created through this process is related to the amount of coeluting compounds. The second pass provides a method in which two peaks having substantially equal apex locations but different shapes to be deconvolved.

Coincidentally with the foregoing, or upon completion of one, some or all of the factor identifications as previously set forth, an average concentration profile is calculated for each factor (S340), see FIG. 10. As an example, 1 multivariate curve resolution (MCR) methods may be employed to determine the average concentration profile for each factor. In an implementation, for one or all of the factors, the calculated average concentration profile is used as an estimated peak shape for each factor. Optionally, the base peak shape may be identified as the estimated peak shape if desired for one or all of the factors. Further, two estimated peak shapes may be used such that the calculated average concentration profile and the base peak shape may be used for one or all of the factors.

Through the use of the average concentration profile, additional undesirable factors can be withdrawn from further calculation by measurement of the peak quality (PQ) of the average concentration profile (S350). In an implementation, PQ may be calculated by a determination of the deviation of the residual of the fit of each concentration profile. Different deviation methods may be employed, for example, a standard deviation in a bi-Gaussian system may be preferably used. In an implementation, a peak quality that is less than a threshold peak quality (e.g., 0.5) is removed from the data and continuing calculations (S360). It is to be appreciated, however, that selection of the PQ threshold and the deviation calculation and methods therefor may be varied depending on the desired results and the invention should not be so limited thereby.

Referring back to FIG. 1, it may be desired to add data back into the factor related to isotopes and adducts (S400). In an implementation, the raw data is reviewed and that data believed to be related to isotopes and adducts is selected and then qualified against all or selected ones of the factors. Qualification to a factor may occur if the data indicates a correlation greater than a minimum correlation having an error rate less than a threshold error rate. In an implementation, the minimum correlation is 0.9 and the error rate is twenty percent. If qualified, the data is then assigned to that factor.

In an implementation, the isotopes/adducts can be identified in the raw data by reviewing typical isotope m/z spacing, and adduct m/z spacing against the raw data and extracting the data indicative of an isotope/adduct based on the review. For example, singly-charged carbon containing compounds have isotope spaced by approximately n*1.003 mass units where n=1, 2, 3, . . . ; in chlorinated compounds, the isotopes are typically spaced by 1.997 mass units. For adducts, if a molecule is ionized using a single sodium ion it will have a mass shift of 21.982 mass units from the same molecule ionized by a single hydrogen ion.

Further, isotopes/adducts of compounds may have been incorrectly grouped with a neighboring coeluting factor (e.g., noise may have caused an isotope/adduct peak to have a higher correlation to a neighbor peak than to its true base peak.) When identified, it may be desirable to reassign such isotopes/adducts. One method to determine and reassign such incorrect grouping is to compare a factor to its neighboring factor(s). In an implementation, the identity of what may constitute a neighboring factor is based on the correlation between the concentration profile of a first factor and that of a proximate factor. If the correlation is greater than a minimum correlation, then the factor is identified as a neighboring factor and potentially containing isotopes or adducts from the first factor. In an implementation, the minimum correlation is 0.9. Next, the neighboring factor is scanned and if isotopes/adducts are qualified as belonging to the first factor, they are reassigned to the first factor. In an implementation, this process may repeated for the next proximate factor until the correlation is less than the minimum correlation. Qualification between a factor and an isotope/adduct may occur if the data indicates a correlation greater than a minimum correlation having an error rate less than a threshold error rate. In an implementation, the minimum correlation is 0.9 and the error rate is twenty percent. If this process empties a factor from all its constituents, that factor is eliminated. This process can be repeated on all or selected portions of the data.

Figure 14:
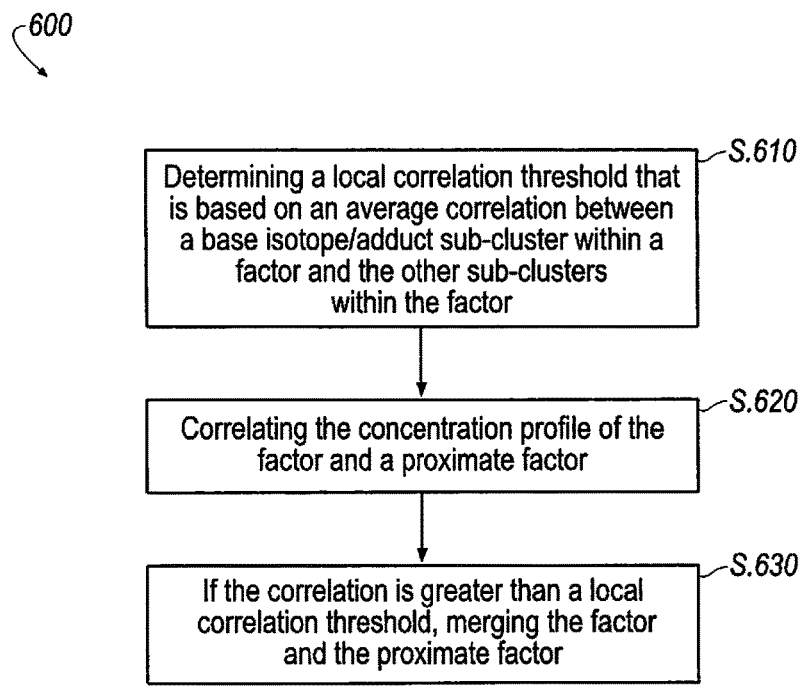
FIG. 14 provides a method to prevent factor splitting.

At times during the process, it may be noticed that that the correlation threshold may be too high. For example, such can occur due to an attempt to deconvolve closely coeluting compounds. However, if the isotopes and adducts are not this highly correlated, factor splitting may result due to an unduly high correlation threshold (i.e., single eluting compounds become modeled by more than one factor). One method to help prevent factor this splitting is shown in FIG. 14. An average of the correlation between a base isotope/adduct sub-cluster within a factor (i.e., most intense) and the other sub-clusters is calculated within that factor, the "local correlation threshold" (S610). Next, a correlation between the concentration profile of a factor and a factor neighboring this factor is determined (S620). If the correlation between the factors is greater than the local correlation threshold, then the two factors are merged (S630). This process may be repeated across all of the factors for each identified base isotope/adduct sub-cluster.

Once a factor is identified and an appropriate estimated concentration profile is selected for a factor, the estimated peak shape is compared with selected curves having known parameters (S370). In an implementation, the estimated concentration profile is normalized and then compared to one or more pre-determined, pre-calculated curves. Normalizing may be provided by stretching or shrinking through a re-sampling procedure and then centered to match the width and center of the pre-calculated curve.

The correlation between the new data and the set of predefined curves is then calculated (S380) and the skew and kurtosis values for the best match are selected as the seed for the optimization (S390).

In an implementation, a Pearson function is used to assign the pre-calculated curves, preferably, a Pearson IV curve. Pearson IV curves may be referenced as having five parameters: (i) height; (ii) center; (iii) width; (iv) skew ($3^{rd}$ moment); and (v) kurtosis ($4^{th}$ moment). In an implementation, the pre-calculated curves are permutations of at least one of the skew and the kurtosis while the remaining parameters are held constant such that the peak shapes are thereafter recorded and saved for each permutation. It is to be appreciated that other permutations may be utilized and the claims should not be so limited to the exemplary implementation disclosed herein. For example, and among others, the height and skew may be varied while holding the center, width and kurtosis and constant values.

It is to be understood that various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

Implementations of the subject matter and the functional operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers.

The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal, that is generated to encode information for transmission to suitable receiver apparatus.

A computer program (also known as a program, software, software application, script, or code) can be written in any form of programming language, including compiled or interpreted languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio player, a Global Positioning System (GPS) receiver, to name just a few. Computer readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

While this specification contains many specifics, these should not be construed as limitations on the scope of the invention or of what may be claimed, but rather as descriptions of features specific to particular implementations of the invention. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

A number of implementations have been described. Nevertheless, it will be understood that various modifications may be made without departing from the spirit and scope of the disclosure. For example, various forms of the flows shown above may be used, with steps re-ordered, added, or removed. Also, although several applications of the systems and methods have been described, it should be recognized that numerous other applications are contemplated. Accordingly, other implementations are within the scope of the following claims.

What is claimed is:

1. A method of identifying information indicative of the presence of ions in a chromatography, mass spectrometry system, the method comprising:
   passing ions through a mass spectrometer and generating data associated therewith in a data acquisition system;
   receiving the data at processing modules;
   processing the data with the processing modules associated with the mass spectrometer to generate processed data, wherein the data includes long clusters and short clusters and the processing step comprises (i) separating, by the processing modules, the long clusters from the short clusters; (ii) filtering, by the processing modules, the data to smooth the data thereby yielding filtered clusters; (iii) dividing, by the processing modules, the filtered clusters into sub-clusters; and (iv) qualifying, by the processing modules, the sub-clusters to extract undesired sub-clusters therefrom;
   analyzing, by the processing modules, the processed data to extract noise therefrom and to group together one or more constituents of the mass spectra for one or more eluting compounds to aid in the elucidation of each of such compounds, wherein the one or more constituents are isotopes, adducts and fragments;

obtaining, by the processing modules, ion information associated with the processed data such that the ion information is free of noise;

preparing and providing, by the processing modules, results relating to the processed data, wherein the results include the ion information.

2. The method of claim 1 further comprising:
reincorporating information associated with at least one of the isotopes and adducts that may have been extracted as noise.

3. The method of claim 1, wherein the separating step further comprises:
separating the data into blocks;
estimating an intensity of a baseline in the center of each block;
linearly interpolating between equidistant quartile points of each block to yield a baseline estimation;
clipping the data above the baseline level and preserving the data below the baseline; and
smoothing the clipped data to yield an improved version of the baseline.

4. The method of claim 3, wherein a length of each block is a multiple of an expected full-width half-height of the data.

5. The method of claim 3, wherein a length of each block is estimated as five times an expected full-width half-height of the data.

6. The method of claim 3, wherein the smoothing step involves the application of a Savitzky-Golay smoothing algorithm.

7. The method of claim 3, wherein estimation of the intensity of a baseline in the center of a block is based on an intensity of the baseline in the lower quartile of the block.

8. The method of claim 1, wherein the qualification step comprises at least one of:
selecting sub-clusters that have a signal-to-noise ratio that is greater than a threshold signal-to-noise ratio
selecting sub-clusters that have a peak shape that is greater than a threshold quality, and
selecting sub-clusters that have a minimum cluster length.

9. The method of claim 8, wherein the threshold signal-to-noise ratio is 10.

10. The method of claim 8, wherein the noise is the pre-defined acquisition noise of one-fourth ($\frac{1}{4}$) ion area.

11. The method of claim 8, wherein the noise is the standard deviation of the residual between the original cluster data and the smoothed cluster data.

12. The method of claim 8, wherein sub-clusters with a signal-to-noise ratio that is less than the threshold signal-to-noise ratio are still used in the factor analysis if they are isotopes or adducts.

13. The method of claim 8, further comprising the step of:
trimming the baseline of a sub-cluster from a left and a right side of a peak.

14. The method of claim 13, wherein the trimming step further comprises:
scanning raw-data within the sub-cluster from the ends to the center;
identifying where the intensities rise above a threshold on each end as a new end point;
discarding the data outside of the new end points.

15. The method of claim 14, wherein the threshold is four times the standard deviation of the sub-cluster.

16. The method of claim 8, wherein the threshold quality is based on a correlation between a fitting of the sub-cluster and a pre-defined curve.

17. The method of claim 16, wherein the pre-defined curve is a bi-Gaussian curve.

18. The method of claim 17, wherein the threshold correlation is 0.8.

19. The method according to claim 18, wherein the defined intensity is at or around one-half of the intensity of one or both of the two peaks.

20. The method of claim 16, wherein the threshold correlation is 0.6.

21. The method of claim 8, wherein the minimum cluster length is 5 sticks.

22. The method of claim 1, wherein the filtering step utilizes an infinite impulse response filter.

23. The method of claim 1, wherein the filtering step comprises:
identifying the largest peak within the data;
estimating the full-width half-height of the identified peak;
matching the estimated full-width half-height against a look-up table to identify one or more optimized filter coefficients;
smoothing the data based on the optimized filter coefficients; and
identifying a noise figure for each cluster.

24. The method of claim 23, wherein the optimized filter coefficients are a set of forward and reverse second-order infinite impulse response filter coefficients.

25. The method of claim 24, wherein the noise figure is the standard deviation of the residual between the smooth data and the raw data.

26. The method of claim 25, wherein the noise figure is assigned to each of the sub-clusters that are derived from a cluster.

27. The method of claim 24, wherein the optimized coefficients are calculated according to the following steps:
forming Gaussian peaks at each expected full-width half-height;
adding noise to the Gaussian peaks thereby yielding noisy Gaussian peaks; and
optimizing the Gaussian peaks to adjust the filter coefficients in a manner that substantially minimizes the residual between the noise Gaussian peaks and the Gaussian peaks.

28. The method of claim 27, wherein the optimizing step utilizes a non-linear Levenburg-Marquardt process.

29. The method of claim 1, wherein the clusters have peaks and valleys and the dividing step further comprises:
identifying each instance within a filtered cluster wherein a valley situated between two peaks has a minimum point that is less than a defined intensity of the two peaks; and
separating the cluster into sub-clusters based on each identified instance, if any.

30. The method according to claim 1, where the analyzing step further comprises:
determining significant factors for factor analysis; and
providing initial seed estimates of those factors.

31. The method according to claim 30, further comprising:
eliminating lower quality peaks.

32. The method according to claim 1, wherein the analyzing step further comprises:
  selecting a base peak among the data;
  evaluating and correlating all local data with the base peak;
  combining local data having a predetermined minimum correlation value with the base peak to create a factor; and
  estimating the spectra for the factor.

33. The method according to claim 32, wherein the base peak is selected manually.

34. The method according to claim 32, wherein the most intense sub-cluster peak in the data set is selected as the base peak.

35. The method according to claim 34, further comprising:
  A) once the base peak is identified, selecting the next most intense peak in the remaining data as the next factor;
  B) upon completion of step (A), selecting the next most intense peak in the remaining data as the next factor; and
  C) repeating step (B) until all sub-clusters are assigned factors.

36. The method according to claim 32, wherein the minimum correlation value is 0.6.

37. The method according to claim 32, further comprising:
  comparing one or both of a correlation threshold and a related confidence interval to separate the local data that was combined in the combining step that should not have been, into separate factors.

38. The method according to claim 37, wherein the comparing step further comprises:
  selecting the most intense sub-cluster in the factor;
  determining a correlation between the base sub-cluster and at least one of the other sub-clusters in the factor;
  determining an apex location confidence interval for at least one of the sub-clusters;
  grouping sub-clusters together that have: (i) overlapping base peaks, and (ii) a correlation to the base peak that is greater than a defined correlation threshold, wherein each of the groupings are factors.

39. The method according to claim 37, further comprising:
  calculating an average concentration profile for each factor.

40. The method according to claim 39, wherein the calculating step utilizes multivariate curve resolution methods to determine the average concentration profile for each factor.

41. The method according to claim 40, wherein the calculated average concentration profile is used as an estimated peak shape for each factor.

42. The method according to claim 41, further comprising:
  comparing the estimated peak shape with at least one pre-selected curve.

43. The method according to claim 42, further comprising normalizing the estimated peak shape prior to the comparing step to define a normalized estimated peak shape.

44. The method according to claim 43, wherein the normalizing step includes at least one of stretching or shrinking through a re-sampling procedure and then centering the estimated peak shape to match the width and center of the at least one pre-selected curves.

45. The method according to claim 43, further comprising:
  calculating a correlation between the normalized peak shape and the at least one pre-selected curve.

46. The method according to claim 45, wherein the skew and kurtosis values for the best match are selected as the seed for the optimization.

47. The method according to claim 42, wherein the at least one pre-selected curves are generated from a Pearson IV function.

48. The method according to claim 47, wherein the at least one pre-selected curves are permutations of at least one of the skew and the kurtosis while the remaining parameters are held constant such that the peak shapes are thereafter recorded and saved for each permutation.

49. The method according to claim 39, further comprising:
  measuring the peak quality of the average concentration profile; and
  removing data having a peak quality less than a threshold peak quality.

50. The method according to claim 49, wherein the measuring step is calculated by a determination of the deviation of the residual of the fit of each concentration profile.

51. The method according to claim 50, wherein the deviation is the standard deviation in a bi-Gaussian system.

52. The method according to claim 49, wherein the threshold peak quality is 0.5.

53. The method according to claim 52, wherein the input correlation parameter is manually entered.

54. The method of claim 37, further comprising:
  identifying isotopes/adducts that are incorrectly grouped with a factor; and
  reassigning such identified isotopes/adducts to a proper factor.

55. The method of claim 54, wherein the identifying step comprises:
  comparing a concentration profile of a factor to a concentration profile of a neighboring factor to identify a correlation;
  if the correlation between the concentration profile of a first factor and that of a neighboring factor is greater than a threshold correlation, reviewing the neighboring factor to located isotopes/adducts from the first factor; and
  reassigning the isotope/adduct to the first factor based on the reviewing step.

56. The method of claim 55, wherein the threshold correlation is 0.9.

57. The method of claim 37, wherein the correlation parameter is user-defined permutation.

58. The method of claim 37, further comprising:
  preventing factor splitting.

59. The method of claim 58, wherein the preventing step comprises:
  determining a local correlation threshold that is based on an average correlation between a base isotope/adduct sub-cluster within a factor and the other sub-clusters within the factor;
  correlating the concentration profile of the factor and a proximate factor; and
  if the correlation is greater than a local correlation threshold, merging the factor and the proximate factor.

60. The method of claim 59, further comprising:
  if a factor is merged, correlation the concentration profile of the factor with the next proximate factor.

61. The method of claim 59, wherein the threshold correlation is 0.9.

62. The method of claim 1 further comprising:
reviewing the data for information associated with one or both of an isotope and an adduct;
selecting the associated data;
qualifying the associated data; and
if the associated data qualifies, assigning it to a factor.

63. The method of claim 62, wherein the qualifying step comprises:
calculating a correlation of the data against a factor; and
if the correlation is greater than the minimum correlation, assigning it to a factor.

64. The method of claim 63, wherein the minimum correlation is 0.9.

* * * * *